(12) United States Patent
Gedet et al.

(10) Patent No.: US 8,771,353 B2
(45) Date of Patent: Jul. 8, 2014

(54) METHOD AND IMPLANT FOR REPLACING DAMAGED MENISCAL TISSUE

(75) Inventors: Philippe Gedet, Oberdorf (CH); Beat Lechmann, Oberdorf (CH); Nicolas Bouduban, Oberdorf (CH)

(73) Assignee: Depuy Synthes Products, LLC, Raynham, MA (US)

( * ) Notice: Subject to any disclaimer, the term of this patent is extended or adjusted under 35 U.S.C. 154(b) by 37 days.

(21) Appl. No.: 13/397,482

(22) Filed: Feb. 15, 2012

(65) Prior Publication Data
US 2012/0232656 A1 Sep. 13, 2012

Related U.S. Application Data

(60) Provisional application No. 61/450,517, filed on Mar. 8, 2011, provisional application No. 61/472,913, filed on Apr. 7, 2011.

(51) Int. Cl.
*A61F 2/08* (2006.01)
*A61F 2/38* (2006.01)
*A61F 2/30* (2006.01)

(52) U.S. Cl.
CPC ........... *A61F 2/3872* (2013.01); *A61F 2/30756* (2013.01)
USPC .................. 623/14.12; 623/20.14; 623/23.76

(58) Field of Classification Search
USPC ...................................................... 623/14.12
See application file for complete search history.

(56) References Cited

U.S. PATENT DOCUMENTS

| | | | |
|---|---|---|---|
| 4,919,667 A | | 4/1990 | Richmond |
| 6,306,169 B1 * | | 10/2001 | Lee et al. .................... 623/11.11 |
| 6,629,997 B2 | | 10/2003 | Mansmann |
| 2005/0234549 A1 * | | 10/2005 | Kladakis et al. ........... 623/14.12 |
| 2005/0278025 A1 * | | 12/2005 | Ku et al. .................... 623/14.12 |
| 2006/0173542 A1 * | | 8/2006 | Shikinami .................. 623/14.12 |
| 2009/0012615 A1 * | | 1/2009 | Fell ............................ 623/14.12 |
| 2009/0171467 A1 * | | 7/2009 | Mann et al. ................ 623/23.63 |
| 2009/0226068 A1 | | 9/2009 | Fitz et al. |
| 2010/0331990 A1 * | | 12/2010 | Mroczkowski et al. ... 623/19.11 |
| 2013/0060334 A1 * | | 3/2013 | Kurzweil ................... 623/14.12 |

FOREIGN PATENT DOCUMENTS

| | | |
|---|---|---|
| EP | 0 053 460 | 6/1982 |
| EP | 2 272 467 | 1/2011 |
| FR | 2635678 A1 * | 3/1990 |
| WO | 2004/075940 | 9/2004 |
| WO | 2005/122966 | 12/2005 |
| WO | 2007/084878 | 7/2007 |

OTHER PUBLICATIONS

International Search Report and Written Opinion (PCT/US2012/025417); Apr. 24, 2012.

* cited by examiner

*Primary Examiner* — David H Willse
*Assistant Examiner* — Javier Blanco
(74) *Attorney, Agent, or Firm* — Dunlap Codding, P.C.

(57) ABSTRACT

A method and apparatus for replacing damaged meniscal tissue includes a meniscus implant including a porous body having a plurality of interconnected open micro-pores and one or more open cavities for receiving meniscal tissue. The interconnected micro-pores are arranged to allow fluid to flow into the porous body and are in fluid communication with the one or more open cavities.

5 Claims, 4 Drawing Sheets

METHOD AND IMPLANT FOR REPLACING DAMAGED MENISCAL TISSUE

CROSS-REFERENCE TO RELATED APPLICATIONS

This application claims priority to U.S. Provisional Application Ser. No. 61/450,517, filed on Mar. 8, 2011, and to U.S. Provisional Application Ser. No. 61/472,913, filed on Apr. 7, 2011, the entire contents of each being hereby expressly incorporated herein by reference.

BACKGROUND

1. Field of the Inventive Concepts

The inventive concepts disclosed herein generally relate to medical implants, and more particularly but not by way of limitation to a meniscus implant for replacing damaged meniscal tissue and to a method for using thereof.

2. Brief Description of Related Art

The menisci are responsible for shock absorption, load transmission, lubrication, and stability of the knee joint. The menisci are important in reducing the incidence of degenerative joint disease. Unfortunately, after trauma or a severe injury the meniscus may be damaged, such as by fissures forming in the meniscus, for example. Damage to the meniscus is associated with changes in joint function that can lead to disability and degenerative joint changes. One of the strategies for meniscal repair suggests the use of biocompatible synthetic or natural scaffolds as a substrate to promote remodeling and healing of the defect. In case of too many fissures, the meniscus may have to be trimmed in a way that only an outer rim of meniscus may be left. A meniscus implant made of a synthetic or natural material may be anchored to the rim via surgical sutures, for example.

The discussion about meniscal repair has been characterized by the debate of meniscectomy (i.e., partial or complete removal of the native meniscus) versus meniscal repair. It has been shown that meniscectomy increases the risk of developing osteoarthritis of the knee joint. Whenever possible, native meniscus tissue should be preserved by surgically sewing and reshaping it to avoid loss of joint stability and the concentration of mechanical forces on the articular cartilage of the femoral condyle and the tibia plateau. In cases where a meniscectomy is inevitable, two different types of meniscus implants are available on the market. One is a fully-synthetic solution and the other is a natural solution based for example on purified Type-I collagen fibers. The synthetic and the natural solution are scaffolds with a porous structure to promote tissue ingrowth. Both concepts are based on the anchorage to the rim and to the posterior and anterior horn of the meniscus with sutures or a dowel-like device.

An example on the market in the category of natural solutions is Menaflex™, formerly CMI, from ReGen Biologics (ReGen Biologics Inc., 411 Hackensack Avenue, Hackensack, N.J. 07601, USA). The Menaflex™ collagen The meniscus implant is a resorbable collagen-based surgical mesh composed primarily of Type-I collagen. It serves to reinforce damaged or weakened meniscus tissue and provides a resorbable scaffold for replacement by the patient's own tissue. Menaflex™ is intended for use in patients with an irreparable meniscus tear, or loss of meniscus tissue. An example in the category of synthetic implant is Actifit™ from Orteq Bioengineering (Orteq Ltd, 10 Greycoat Place, London, SW1P 1SB, United Kingdom). Actifit™ is a resilient, flexible, highly porous, and biocompatible synthetic scaffold. Its structure comprises open continuous pores, through which blood vessels can rapidly grow into the implant. The blood transports cells and nutrients that initiate the growth of new meniscus-like tissue inside the synthetic scaffold.

BRIEF SUMMARY OF THE INVENTIVE CONCEPTS

In one embodiment, the present disclosure relates to a method for replacing damaged meniscal tissue using a meniscus implant including a porous body with interconnected open micro-pores and one or more open cavities for receiving native meniscus material. More specifically, one method comprises the steps of:

A) performing an incision permitting a surgical access to at least one of the menisci in a knee joint;
B) cutting away a portion of a native meniscus so that a rim of native meniscus material at the outer convex side of the native meniscus remains;
C) selecting a meniscus implant of a desired size and having one or more open cavities;
D) obtaining one or more pieces of the native meniscus;
E) inserting the pieces into the cavities of the meniscus implant;
F) inserting the meniscus implant including the pieces between a respective femoral condyle and the tibial plateau in a patient's knee joint so that the outer convex peripheral surface of the porous body abuts the inner concave side of the rim of remaining native meniscus material;
G) fixing the meniscus implant to the rim of native meniscus material; and
H) closing the incision.

The meniscus implant may be fixed to the rim of native meniscus material with a plurality of suture loops. Alternatively, the meniscus implant can be fixed to the rim of native meniscus material by a dowel like device.

The concept of this meniscus implant, which can be made of a porous synthetic material, is based on empty spaces or cavities which can be filled with native meniscus material that was recuperated during the trimming procedure.

In one embodiment of the method, the porous body may be C-shaped and comprise between about 1 and about 10 open cavities.

In another embodiment of the method, the pieces of native meniscus are punched out of the cut away portion of the patient's native meniscus. Alternatively, native meniscus material from a donor can be used.

In another embodiment of the method, the pieces of meniscus are cylindrical or prismatical.

In yet another embodiment, the method further comprises before step D) the substep of:

trimming the meniscus implant to a desired shape.

By this means the advantage can be achieved that the meniscus implant can have a pre-operative shape of a complete meniscus, so that the same meniscus implant could be used in the case of a total meniscectomy as well. However, in most cases the native meniscus is only partly cut away so that a meniscal rim is maintained.

In a further embodiment of the method:

under step C) a meniscus implant is selected where the cavities of the porous body have a diameter d; and
under step D) a punching die is used that has a bore with a diameter $D_i$ that is greater than d so that the pieces that are punched out of the cut away native meniscus material can be fixed in the cavities by a press fit.

In a further embodiment of the method under step C) a meniscus implant is selected where the cavities penetrate through the porous body from the upper surface to the lower surface of the porous body and wherein the porous body further comprises transverse passages penetrating through the porous body and through the cavities from the outer convex peripheral surface to the inner concave peripheral surface.

In a further embodiment, the method further comprises before step F) the substep of:

fixing the pieces of meniscus within the cavities of the porous body by leading a suture through the transverse passages and through the pieces, preferably in the middle of the height of the pieces.

In a still further embodiment of the method, the suture is subsequently led through the transverse passages and through the pieces in a meander line. Therewith, the advantage can be achieved that the suture can be firmly tightened and two knots at the ends of the suture only are necessary.

In yet a further embodiment of the method under step C) a meniscus implant is selected where the cavities penetrate into the porous body from the outer convex peripheral surface in the form of pocket holes.

In another embodiment, the method further comprises before step F) the substep of:

fixing the pieces of meniscus within the cavities of the porous body by gluing the pieces into the cavities.

In an alternative embodiment the method further comprises before step F) the substep of:

fixing the pieces within the cavities of the porous body by gluing a grid or a membrane on the outer convex peripheral surface over each cavity.

In again another embodiment of the method step G) further comprises the substeps of:

drilling a bore hole from a side surface of the tibia through the tibial plateau at the former attachment site of a horn of the native meniscus; and fixing a horn of the meniscus implant to the tibia with a thread lead through the bore hole or with a stopper attached to a horn of the meniscus implant and pressed into the bore hole.

In yet another embodiment of the method, the interconnected pores of the porous body are filled with a hydrogel-like substance containing cells.

According to a further aspect of the present disclosure, there is provided a meniscus implant for replacing damaged meniscal tissue including a porous body with a central axis; the porous body comprising: a) an outer convex peripheral surface and an inner concave peripheral surface; b) an upper surface and a lower surface; and c) a cross-sectional area orthogonal to the central axis and tapering towards the inner concave peripheral surface, wherein d) the porous body comprises interconnected open micro-pores; and e) the porous body comprises one or more open cavities.

In one embodiment of the meniscus implant, the porous body is C-shaped and comprises a plurality of cavities either regularly or irregularly distributed over the porous body.

In another embodiment of the meniscus implant, the one or more cavities may have a minimum diameter of about 1.5 mm, and preferably about 2.0 mm.

In another embodiment of the meniscus implant, the one or more cavities may have a maximum diameter of about 5.5 mm, and preferably about 5.0 mm.

In again another embodiment of the meniscus implant, the cavities penetrate through the porous body from an upper surface to a lower surface.

In a further embodiment of the meniscus implant, the cavities are cylindrical or prismatical and have a longitudinal axis each that extends essentially orthogonally to the lower surface of the porous body.

In a further embodiment of the meniscus implant, the cavities penetrate into the porous body from the outer convex peripheral surface in the form of pocket holes.

In again another embodiment of the meniscus implant, the porous body further comprises transverse passages penetrating through the porous body and through the cavities from the outer convex peripheral surface to the inner concave peripheral surface.

In still another embodiment of the meniscus implant, the porous body comprises interconnected pores that are open at the outer convex peripheral surface, at the inner concave peripheral surface, at the upper surface, and at the lower surface so as to promote cellular in-growth.

In a further embodiment of the meniscus implant, the micro-pores have a minimum diameter of about 120 µm, and preferably about 150 µm.

In again a further embodiment of the meniscus implant, the micro-pores have a maximum diameter of about 370 µm, and preferably about 355 µm.

In another embodiment of the meniscus implant, the porous body is made of a material with an elastic modulus in tension $E_{ci}$ of at least about 10 MPa measured in a circumferential direction, an elastic modulus in tension $E_r$ of at least about 1 MPa measured in a radial direction, and an elastic modulus in compression $E_{co}$ of at least about 0.1 MPa. Typical ranges can be for the elastic modulus in tension measured in a circumferential direction $E_{ci}$ between about 10 MPa and about 300 MPa, the elastic modulus in tension measured in a radial direction $E_r$ between about 1 MPa and about 10 MPa and the elastic modulus in compression $E_{co}$ between about 0.1 MPa and about 1.0 MPa.

In still another embodiment of the meniscus implant, the porous body is made of a synthetic material, preferably of polyurethane.

In yet another embodiment of the meniscus implant, the interconnected pores of the porous body are filled with a hydrogel-like substance containing cells.

For example and without limitation, the meniscus implant can be used for replacement of a native meniscus.

In accordance with another aspect, a meniscus implant is provided comprising a porous body with a central axis; the porous body comprising:

I) an outer convex peripheral surface and an inner concave peripheral surface;

II) an upper surface and a lower surface; and

III) a cross-sectional area orthogonal to the central axis and tapering towards the inner concave peripheral surface, wherein IV) the porous body comprises a number M of spikes protruding from the outer convex peripheral surface of the porous body to permit the meniscus implant to be attached to the native rim.

In another embodiment of the meniscus implant, the porous body comprises cannulations penetrating through the spikes and into the porous body towards the inner concave peripheral surface so as to permit blood flow into the meniscus implant.

In a further embodiment of the meniscus implant, the cannulations have a minimum diameter of about 0.4 mm, and preferably about 0.45 mm.

In again a further embodiment of the meniscus implant, the cannulations have a maximum diameter of about 1.0 mm, and preferably about 0.55 mm.

In another embodiment of the meniscus implant, the porous body comprises micro-pores with a minimum diameter of about 120 µm, and preferably about 150 µm.

In another embodiment of the meniscus implant, the porous body comprises micro-pores with a maximum diameter of about 370 μm, and preferably about 355 μm.

In yet another embodiment of the meniscus implant, the porous body is made of a material with an elastic modulus in tension $E_{ct}$ of at least about 10 MPa measured in a circumferential direction, an elastic modulus in tension $E_r$ of at least about 1 MPa measured in a radial direction and an elastic modulus in compression $E_{co}$ of at least about 0.1 MPa. Typical ranges can be for the elastic modulus in tension measured in a circumferential direction $E_{ct}$ between about 10 MPa and about 300 MPa, the elastic modulus in tension measured in a radial direction $E_r$ between about 1 MPa and about 10 MPa and the elastic modulus in compression $E_{co}$ between about 0.1 MPa and about 1.0 MPa.

In again another embodiment of the meniscus implant, the porous body is made of a synthetic material, such as polyurethane.

In still another embodiment of the meniscus implant, the number M of spikes is between about 1 and about 10.

In a further embodiment of the meniscus implant the interconnected pores of the porous body are filled with a hydrogel-like substance containing cells.

BRIEF DESCRIPTION OF THE DRAWINGS

Like reference numerals in the figures represent and refer to the same or similar element or function. Implementations of the inventive concepts disclosed herein may be better understood when consideration is given to the following detailed description thereof. Such description makes reference to the annexed pictorial illustrations, schematics, graphs, drawings, and appendices. In the drawings.

DETAILED DESCRIPTION OF EXEMPLARY EMBODIMENTS

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description only and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein the notation "a-n" appended to a reference numeral is intended as merely convenient shorthand to reference one, or more than one, and up to infinity, of the element or feature identified by the respective reference numeral (e.g., 134a-n). Similarly, a letter following a reference numeral is intended to reference an embodiment of the feature or element that may be similar, but not necessarily identical, to a previously described element or feature bearing the same reference numeral (e.g., 148, 148a, 148b, etc.). Such shorthand notations are used for purposes of clarity and convenience only, and should not be construed to limit the instant inventive concept(s) in any way, unless expressly stated to the contrary.

Further, unless expressly stated to the contrary, "or" refers to an inclusive "or" and not to an exclusive "or." For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 1:
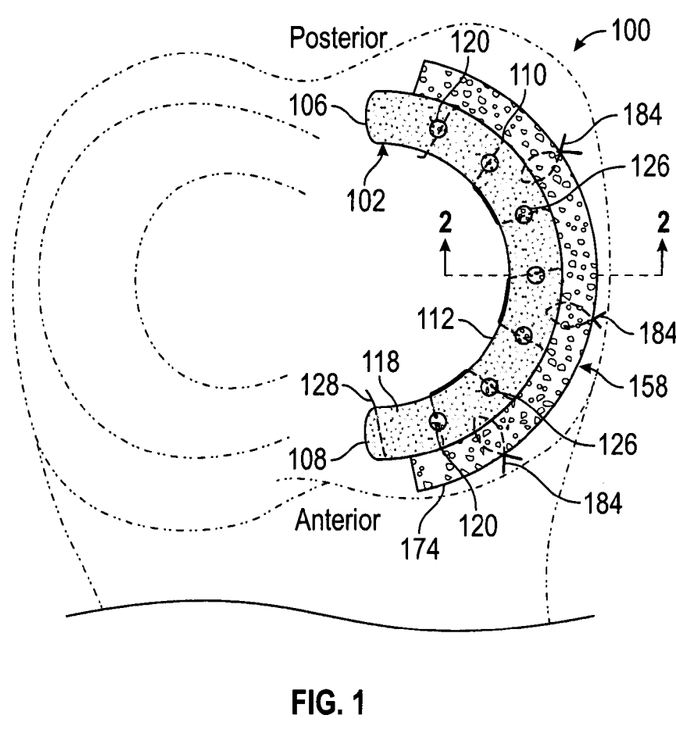
FIG. 1 is a top view of an exemplary embodiment of a meniscus implant according to the inventive concepts disclosed herein shown fixed to a rim of native meniscus material.
Figure 2:
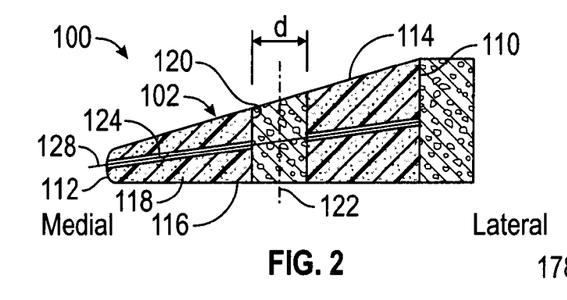
FIG. 2 is a sectional view taken along line 2-2 of FIG. 1.

Referring now to the drawings, and more particularly to FIGS. 1 and 2, a meniscus implant 100 for replacing damaged meniscal tissue is illustrated attached to a rim 101 of native meniscus. The meniscus implant 100 includes a porous body 102 with a first end 106 and a second end 108. The first end 106 may be referred to as a posterior horn, and the second end 108 may be referred to as anterior horn, for example. The porous body 102 further has an outer convex peripheral surface 110, an inner concave peripheral surface 112, an upper surface 114, and a lower surface 116. As shown in FIG. 2, the porous body 102 has a cross-sectional area in a plane orthogonal to the lower surface 116 which tapers to the inner concave peripheral surface 112.

The lower surface 116 of the porous body 102 may be planar. The upper surface 114 can be a part of a conical surface or can be concavely curved, for example. The outer convex peripheral surface 110 can be orthogonal to the lower surface 116 of the porous body 102. The upper surface 114 may taper such that the porous body 102 has a first height at the outer convex peripheral surface 110 and a second height at the inner concave peripheral surface 112, each measured orthogonally to the lower surface 116 of the porous body 102. The first height measured at the outer convex peripheral surface 110 and/or the second height measured at the inner concave peripheral surface 112 can be constant between the first end 106 and the second end 108. Alternatively, the first height of the porous body 102 measured at the outer convex peripheral surface 110 and/or the second height measured at the inner concave peripheral surface 112 of the porous body 102 can increase or decrease towards the first end 106 and the second end 108 of the porous body 102.

The porous body 102 further comprises one or more interconnected micro-pores 118 which are open at the outer convex peripheral surface 110, at the inner concave peripheral surface 112, at the upper surface 114, and at the lower surface 116. The interconnected micro-pores 118 may have a diameter between about 120 μm and about 370 μm, for example. The interconnected micro-pores 118 of the porous body 102 may be filled with a hydrogel-like substance containing cells (not shown).

The porous body 102 may be substantially C-shaped and may have a plurality of open cavities 120 formed therein. FIG. 1 illustrates the meniscus implant 100 as having nine open cavities 120, but it will be appreciated that the number may be varied. The open cavities 120 can be cylindrical or prismatical, and may have a longitudinal axis 122 that extends essentially orthogonally to the lower surface 116 of the porous body 102, so that the longitudinal axes 122 of the open cavities 120 extend in the cranio-caudal direction and in a plurality of sagittal planes. For example, as illustrated in FIG. 1, the open cavities 120 can be arranged in such a way that the longitudinal axis 122 of the open cavities 120 are equally spaced along the porous body 102. The open cavities 120 may each have a diameter between about 2.0 mm and about 5.0 mm. Alternatively, the open cavities 120 can be distributed irregularly over the porous body 102.

The porous body 102 may further comprise transverse passages 124 penetrating through the porous body 102 and through the open cavities 120 from the outer convex peripheral surface 110 to the inner concave peripheral surface 112. Each transverse passage 124 intersects one of the open cavities 120, preferably in the middle of the height of the respective open cavity 120. Pieces of native meniscus material 126 can be fixed within the open cavities 120 of the porous body 102 by a press fit, and additionally by leading a suture 128 through the transverse passages 124 and through the pieces of native meniscus material 126 inserted in the open cavities 120. The open cavities 120 can be regularly distributed over the porous body 102.

Figure 9A:
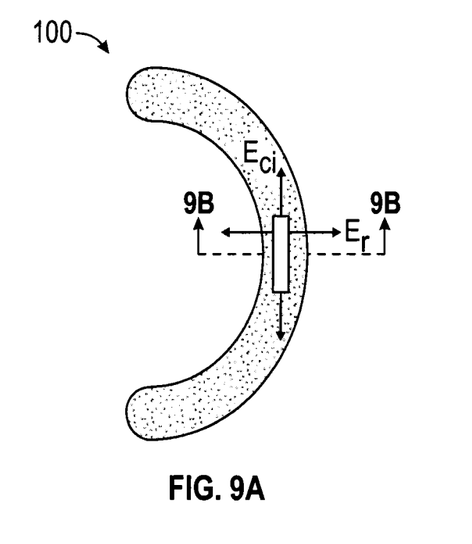
FIG. 9A illustrates a top view of an exemplary embodiment of a meniscus implant according to the inventive concepts disclosed herein with indication of the measuring direction of the elastic moduli in tension.
Figure 9B:
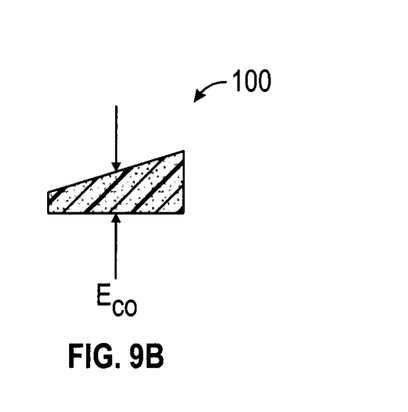
FIG. 9B is a cross-sectional view taken along line 9B-9B of FIG. 9A with indication of the measuring direction of the elastic modulus in compression.

The porous body 102 can be made of a synthetic material, e.g., a polyurethane with an elastic modulus in tension measured in a circumferential direction $E_{ci}$ between about 10 and about 300 MPa, an elastic modulus in tension measured in a radial direction $E_r$ between about 1 and about 10 MPa, and an elastic modulus in compression $E_{co}$ between about 0.1 and about 1.0 MPa (FIGS. 9A-9B).

Figure 4:
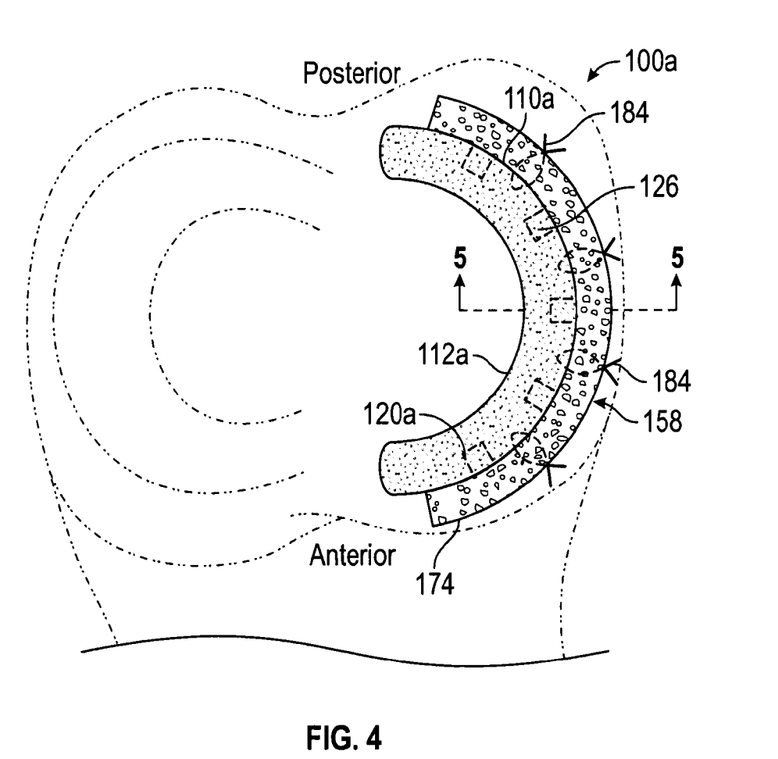
FIG. 4 is a top view of another embodiment of a meniscus implant according to the inventive concepts disclosed herein shown fixed to a rim of native meniscus material.
Figure 5:
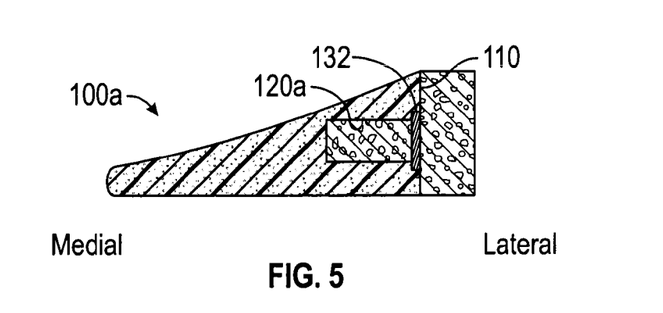
FIG. 5 is a sectional view taken along line 5-5 of FIG. 4.

Referring now to FIGS. 4-5, another embodiment of a meniscus implant 100a may be substantially similar to the meniscus implant 100 of FIGS. 1 and 2, except the meniscus implant 100a includes a porous body 102a with a plurality of cavities 120a arranged in such a way that a longitudinal axis of the cavities 120a extend in a transverse plane of the human body and that the porous body 102a has no transverse passages. The open cavities 120a penetrate into the porous body 102a from the outer convex peripheral surface 110a in the form of pocket holes 130. Alternatively, the open cavities 120a can be staggered so that their longitudinal axes can extend, e.g., alternatingly in two or more transverse planes. Pieces of native meniscus material 126 can be fixed within the open cavities 120a of the porous body 102a by gluing a grid or a membrane 132 on the outer convex peripheral surface 110a over each open cavity 120a. Alternatively, the pieces of native meniscus material 126 can be glued directly into the open cavities 120a.

In another embodiment, the porous body 102a can comprise transverse passages penetrating through the porous body 102a and through the open cavities 120a from the outer convex peripheral surface 110a to the inner concave peripheral surface 112a similarly to the embodiment of FIGS. 1-2. Each transverse passage can intersect one of the open cavities 120a, preferably in the middle of the height or diameter of the respective open cavity 120a. Therefore, pieces of native meniscus material 126 can be additionally fixed within the open cavities 120a of the porous body 102a by a press fit and by leading a suture through the transverse passages and through the pieces of native meniscus material 126 inserted in the open cavities 120a.

Figure 6:
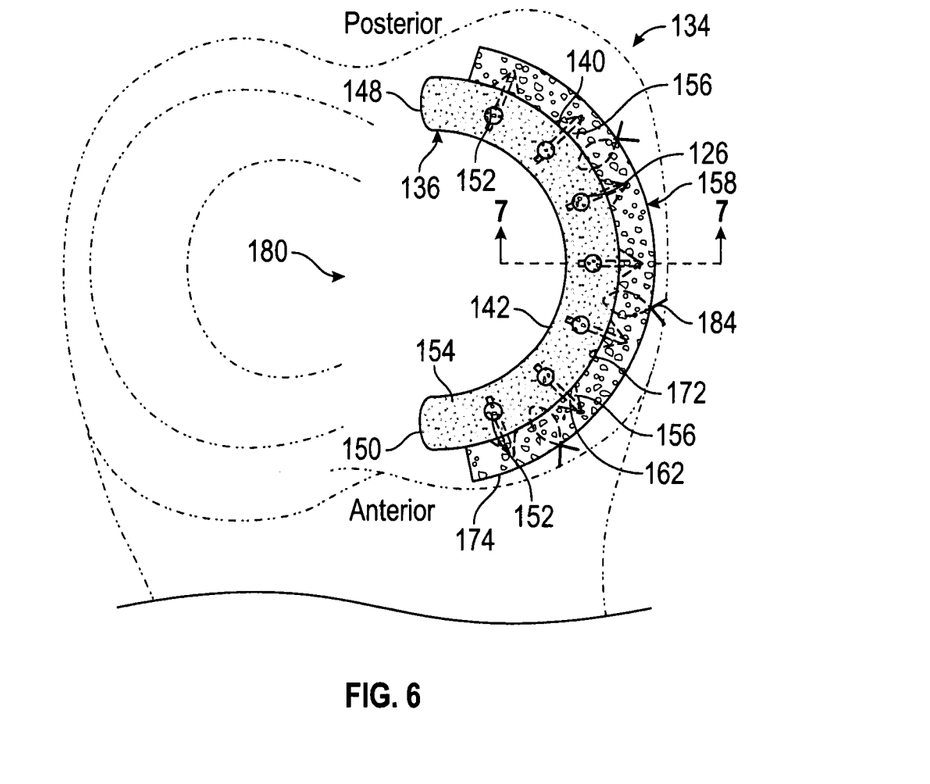
FIG. 6 is a top view of another embodiment of a meniscus implant according to the inventive concepts disclosed herein shown fixed to a rim of native meniscus material.
Figure 7:
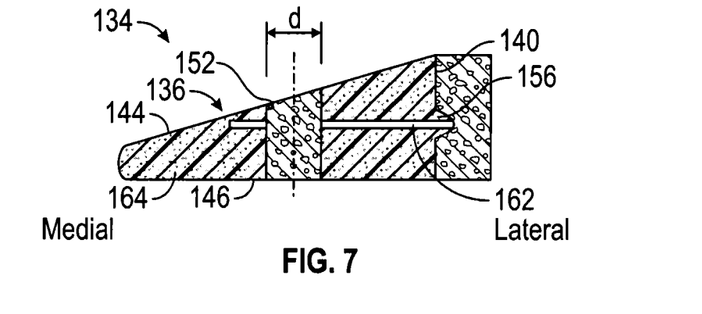
FIG. 7 is a sectional view taken along line 7-7 of FIG. 6.

Another embodiment of a meniscus implant 134 is illustrated in FIGS. 6-7. The meniscus implant 134 includes a porous body 136 with an outer convex peripheral surface 140, an inner concave peripheral surface 142, an upper surface 144, and a lower surface 146. In one embodiment, the porous body 136 may be C-shaped, as shown. However, the porous body 136 may be formed into any desired shape. The porous body 136 has a cross-sectional area orthogonal to the lower surface 146 which tapers towards the inner concave peripheral surface 142. The lower surface 146 of the porous body 136 is substantially planar.

The upper surface 144 can be a part of a conical surface or can be concavely curved. The outer convex peripheral surface 140 can be orthogonal to the lower surface 146 of the porous body 136. The porous body 136 can have a height at the outer convex peripheral surface 140 and a height at the inner concave peripheral surface 142 each measured orthogonally to the lower surface 146 of the porous body 136. The height measured at the outer convex peripheral surface 140 and/or the height measured at the inner concave peripheral surface 142 can be constant between a first end 148 and a second end 150. Alternatively, the height of the porous body 136 measured at the outer convex peripheral surface 140 and/or the height measured at the inner concave peripheral surface 142 of the porous body 136 can increase or decrease towards the first end 148 and second end 150 of the porous body 136.

Similar to the porous body 102 described above, the porous body 136 is shown to have a plurality of open cavities 152 in which pieces of native meniscus material 126 may be fixed in a manner described above. It will be understood that the open cavities 152 may also be arranged in a manner similar to that shown in FIGS. 4-5 with respect to the open cavities 120a.

The porous body 136 may comprise one or more open interconnected micro-pores 154 which may have a diameter between about 120 μm and about 370 μm. The interconnected micro-pores 154 of the porous body 136 can be filled with a hydrogel-like substance containing cells.

Furthermore, the porous body 136 has a plurality of spikes 156 protruding from the outer convex peripheral surface 140 of the porous body 136 to facilitate attachment of the meniscus implant 134 to the native rim 158. The spikes 156 can have the shape of truncated cones or truncated pyramids. The spikes 156 may be arranged in such a way that their central axes extend in a direction essentially parallel to the lower surface 146 of the porous body 136 and extend from the outer convex peripheral surface 140 in a radial pattern when viewed from a top view. The spikes 156 can be regularly or irregularly distributed over the outer convex peripheral surface 14 of the porous body 136. For example, the spikes 156 may be located at a height measured from the lower surface 152 of the porous body 136 which can be in range of about 35% to about 55% of the height of the outer convex peripheral surface 146 of the porous body 136, for example.

The porous body 136 may further include cannulations 162 extending through the spikes 156 to facilitate blood flow to the porous body 136. The cannulations 162 can have a diameter between about 0.4 mm and about 1.0 mm, for example.

The porous body 136 can be made of a synthetic material, e.g., a polyurethane with an elastic modulus in tension measured in a circumferential direction $E_{ct}$ between about 10 to about 300 MPa, an elastic modulus in tension measured in a radial direction $E_r$ between about 1 to about 10 MPa and an elastic modulus in compression $E_{co}$ between about 0.1 and about 1.0 MPa (FIGS. 9A and 9B).

Figure 3:
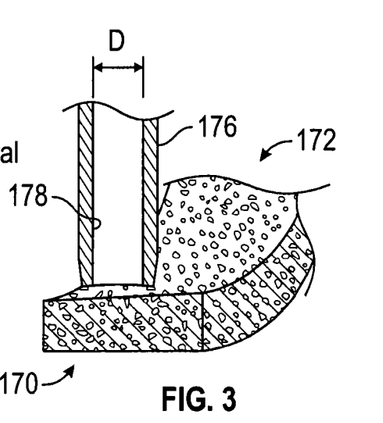
FIG. 3 is a cut away view of a portion of a native meniscus and a sectional view of a punching tool used in an embodiment of the method according to the inventive concepts disclosed herein.

A first embodiment of a method for replacing damaged meniscal tissue can be performed by using the embodiment of the meniscus implant 100 according to FIGS. 1-3. An incision permitting a surgical access to at least one of the menisci in a knee joint may be performed, and a portion 170 of a native meniscus 172 (FIG. 3) may be cut away so that a rim 158 of native meniscus material at an outer convex side 174 of the native meniscus 172 remains. Then, a meniscus implant 100 of a desired size and having a desired number N of open cavities 120 is selected.

As illustrated in FIG. 1, the meniscus implant 100 may comprise a porous body 102 with exemplarily N=9 open cavities 120 with a longitudinal axis 122 each. The meniscus implant 100 comprises open cavities 120 penetrating through the porous body 102 from the upper surface 114 to the lower surface 116 so that the open cavities 120 are arranged with their longitudinal axes 122 extending in a cranio-caudal direction. Exemplarily, the open cavities 120 of the porous body 102 are circular cylindrical and have a first diameter d. Further, the porous body 102 can comprise transverse passages 124 penetrating through the porous body 102 and through the open cavities 120 from the outer convex peripheral surface 110 to the inner concave peripheral surface 112. If necessary the meniscus implant 100 can be trimmed to a desired shape by using, e.g., a chisel.

A number N of pieces of native meniscus material 126 may be punched out of the native meniscus 172. The open cavities 120 of the porous body 102 can then be filled with material gained from the meniscectomy. The pieces of native meniscus material 126 are preferably punched out of the cut away portion 170 of the patient's native meniscus 172, e.g., by using a punching die 176 that has a bore 178 with a second diameter D that is larger than the first diameter d of the open cavities 120. Then, a piece of native meniscus material 126 is inserted into each open cavity 120 in the meniscus implant 100. Because the pieces of native meniscus material 126 have a second diameter D which is larger than the first diameter d of the open cavities 120, the pieces of native meniscus material 126 are at least partially fixed in the open cavities 120 by a press fit.

The pieces of native meniscus material 126 can be further fixed within the open cavities 120 by leading a suture 128 through the transverse passages 124 and through the pieces of native meniscus material 126, preferably in the middle of the height of the pieces of native meniscus material 126. The suture 128 can be successively led through the transverse passages 124 and through the pieces of native meniscus material 126 in a meander line and may be firmly tightened with a knot at each end, or otherwise secured. The pieces of native meniscus material 126 are then additionally fixed to the porous body 102 by means of the suture 128 running through the transverse passages 124 and penetrating the pieces of native meniscus material 126 in the middle of their height, for example. The material from the native meniscus 172 is so held in place not only via this suture 128, but as well by the press fit, which is obtained by using the punching die 176 with a larger inner diameter than the diameter of the open cavity 120. This press fit may mimic the existence of pre-stresses during in vivo remodeling.

Afterwards, the meniscus implant 100 including the pieces of native meniscus material 126 may be inserted between a femoral condyle (not shown) and the tibial plateau 180 in a patient's knee joint, so that the outer convex peripheral surface 110 of the porous body 102 abuts the inner concave side 182 of the rim 158 of remaining native meniscus 172 material. Then the meniscus implant 100 can be fixed to the rim 140 of native meniscus 172 material with a plurality of suture loops 184 wherein each suture loop 184 is led through the porous body 102 and the rim 158 of native meniscus 172 material. Finally, the incision may be closed.

Figure 8:
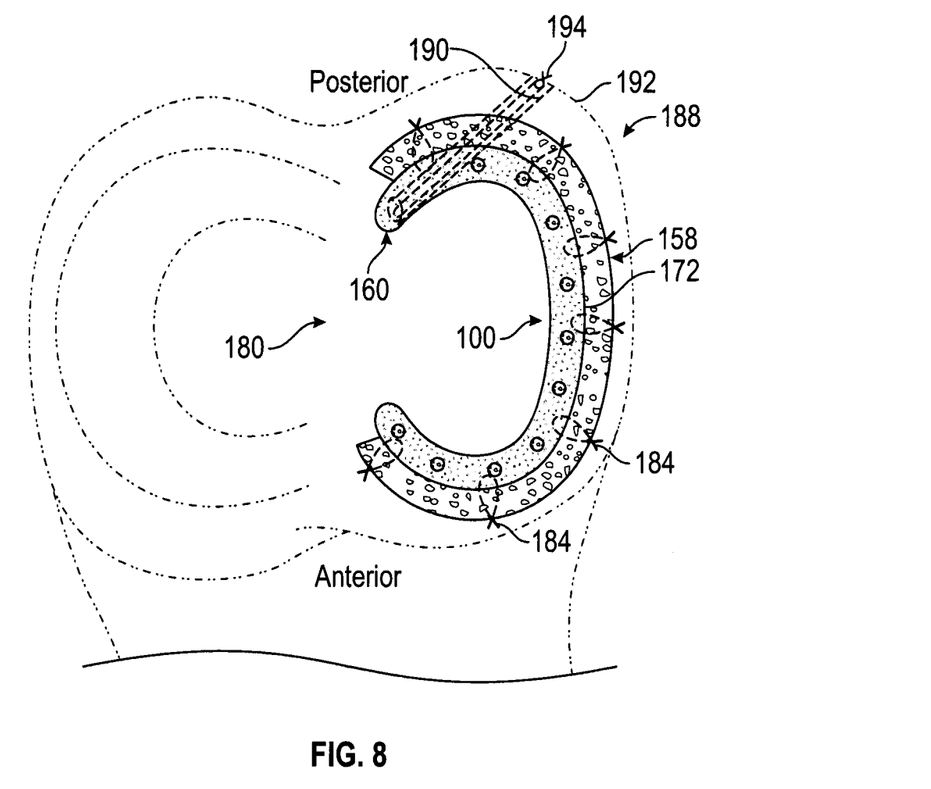
FIG. 8 is a top view of a tibial plateau with an exemplary embodiment of a meniscus implant according to the inventive concepts disclosed herein attached to the tibia in the area of the posterior horn of the meniscus implant.

If the entire native meniscus 170, except the rim 158 has to be removed, an additional fixation of the first end 106 and the second end 108 of the meniscus implant 100 may be necessary. As illustrated in FIG. 8, the fixation of the first end 106 of the meniscus implant 100 to the tibia 188 can be effected via a bore hole 190 that is drilled from the peripheral wall 192 of the tibia 188 and through the tibial plateau 180 at the former attachment site of the posterior or anterior horn of the native meniscus 172. The first end 106 of the meniscus implant 100 can then be affixed to the tibia 188 by a thread 194 that is led through the bore hole 190 and anchored at the peripheral wall 192 of the tibia 188, e.g., by a knot. Alternatively, the fixation of the second end 108 and/or first end 106 of the meniscus implant 100 can be realized with plug-like fixation devices which are pressed into the tibial plateau 180.

A second embodiment of the method for replacing damaged meniscal tissue can be performed by using the embodiment of the meniscus implant 100a according to FIGS. 4-5. This second embodiment of the method differs from the first embodiment in that the meniscus implant 100a according to the embodiment of FIGS. 4-5 is selected and that the fixation of the pieces of native meniscus material 126 in the open cavities 120a is effected via a grid or membrane 132 which is fixed to the porous body 102a after insertion of the pieces of native meniscus material 126 in the open cavities 120a. The meniscus implant 100a illustrated in FIG. 4 exemplarily comprises N=5 open cavities 120a that are arranged in such a way that the longitudinal axes of the N=5 open cavities 120a extend in a transverse plane of the human body. The open cavities 120a penetrate into the porous body 102a from the outer convex peripheral surface 110a so that a lateral opening 164 of each open cavity 120a faces the rim 158 of the trimmed meniscus after meniscectomy. The open cavities 120a are in the form of pocket holes. The pieces of native meniscus material 126 can be fixed within the open cavities 120a of the porous body 102a, e.g., by gluing a grid or a membrane 132 on the outer convex peripheral surface 110a over each open cavity 120a, or can be fixed within the open cavities 120a by gluing only, for example. In an alternative embodiment, the porous body 102a can comprise transverse passages similar to transverse passages 124 of the porous body 102, penetrating through the porous body 102a and through the open cavities 120a from the outer convex peripheral surface 110a to the inner concave peripheral surface 112a. The pieces of native meniscus material 126 can be additionally fixed within the open cavities 120a of the porous body 102a by a press fit and/or by leading a suture through the transverse passages and through the pieces of native meniscus material 126 inserted in the open cavities 120a.

Similarly to the first embodiment of the method, an additional fixation of the first end 106 and/or the second end 108 of the meniscus implant 100a can be necessary if the entire native meniscus except the rim 158 has to be removed as exemplarily illustrated in FIG. 8 for a fixation of the first end 106a of the meniscus implant 100a to the tibia 188.

FIGS. 9A-9B schematically illustrate the measuring directions of the elastic moduli in tension $E_{ci}$; $E_r$, and the elastic modulus in compression E. The following definitions apply for the porous bodies 102 and 102a of the meniscus implants 100 and 100a according to each of the embodiments of FIGS. 1-5 as well as for the porous body 136 of the meniscus implant 134 according to FIGS. 6-7. $E_{ci}$ is the elastic modulus in tension measured in a direction along the principal fiber, i.e., along the longitudinal axis or in a circumferential direction of the porous body 102, the porous body 102a, and the porous body 136. $E_r$ is the elastic modulus in tension measured in a radial direction of the porous body 102, the porous body 102a, and the porous body 136, i.e., transversely to the principal fiber or circumference and $E_{co}$ is the elastic modulus in compression measured in a direction orthogonal to the lower surface 116 of the porous body 102, the lower surface 116a of the porous body 102a, or the lower surface 146 of the porous body 136.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A meniscus implant for replacing damaged meniscal tissue, comprising:

a substantially C-shaped porous body comprising an outer convex peripheral surface, an inner concave peripheral surface, an upper surface, a lower surface, and a cross-sectional area in a plane orthogonal to the lower surface which tapers from the outer convex peripheral surface to the inner concave peripheral surface, the porous body having a plurality of interconnected open micro-pores arranged to allow fluid to flow into the porous body and a plurality of open cavities equally spaced along the porous body for receiving meniscal tissue, wherein each of the plurality of open cavities penetrates through the porous body from the upper surface to the lower surface, wherein each of the plurality of open cavities having a diameter between about 1.5 mm and about 5.5 mm, wherein the interconnected micro-pores are open at the outer convex peripheral surface, the inner concave peripheral surface, the upper surface, and the lower surface, the micro-pores having a diameter between about 120 µm and about 370 µm, wherein the interconnected micro-pores are in fluid communication with the plurality of open cavities, wherein the porous body further comprises one or more transverse passages penetrating through the porous body and through the cavities from the outer convex peripheral surface to the inner concave peripheral surface.

2. The meniscus implant 1, wherein the cavities are cylindrical or prismatical and have a longitudinal axis each that extends essentially orthogonally to the lower surface of the porous body.

3. The meniscus implant of claim 1, wherein the porous body is made of a material with an elastic modulus in tension $E_{ci}$ of minimum of about 10 MPa measured in a circumferential direction, an elastic modulus in tension $E_r$ of minimum about 1 MPa measured in a radial direction, and an elastic modulus in compression $E_{co}$ of minimum of about 0.1 MPa.

4. The meniscus implant of claim 3, wherein the porous body is made of a synthetic material.

5. The meniscus implant of claim 1, wherein the interconnected micro-pores of the porous body are filled with a hydrogel-like substance containing cells.

* * * * *